(12) United States Patent
Hoshino et al.

(10) Patent No.: US 7,670,814 B2
(45) Date of Patent: Mar. 2, 2010

(54) MICROBIAL PRODUCTION OF VITAMIN C

(75) Inventors: Tatsuo Hoshino, Kamakura (JP); Teruhide Sugisawa, Riehen (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/587,333

(22) PCT Filed: Jan. 22, 2005

(86) PCT No.: PCT/EP2005/000622

§ 371 (c)(1),
(2), (4) Date: Sep. 8, 2006

(87) PCT Pub. No.: WO2005/075658

PCT Pub. Date: Aug. 18, 2005

(65) Prior Publication Data

US 2007/0161093 A1 Jul. 12, 2007

(30) Foreign Application Priority Data

Jan. 30, 2004 (EP) .................... 04002074

(51) Int. Cl.
*C12P 1/04* (2006.01)
*C12P 17/04* (2006.01)
*C12P 1/00* (2006.01)

(52) U.S. Cl. .................... 435/170; 435/126; 435/41

(58) Field of Classification Search .................... 435/41, 435/170
See application file for complete search history.

(56) References Cited

U.S. PATENT DOCUMENTS 4,935,359 A * 6/1990 Yin et al. .................... 435/138
5,834,231 A 11/1998 Stoddard et al.
6,316,231 B1 * 11/2001 Stoddard et al. ............ 435/138

OTHER PUBLICATIONS

NCBI (National Center for Biotechnology Information), Taxonomy Browser (Ketogulonicigenium vulgare), [Retrieved on Feb. 15, 2008], Retrieved from Internet: <http://www.ncbi.nlm.nih.gov/Taxonomy/Browser/wwwtax.cgi?mode=Info&id=92945&lvl>.*
Sugisawa et al., 2005, Biosci. Biotechnol. Biochem., 69, 659-662.*
Asakura et al., 1999, Biosci. Biotechnol. Biochem., 63, 46-53.*
Urbance et al, "Taxonomic characterization of *Ketogulonigenium vulgare* gen. nov., sp. Nov. and *Ketogulonigenium robustum* sp. Nov., which oxidize L-sorbose to 2-keto-L-gulonic acid", International Journal of Systemic and Evolutionary Microbiology, Society for General Microbiology, Reading., GB, vol. 51, No. 3, May 2001, pp. 1059-1070.
Leduc et al, "Folate requirements of the 2-keto-L-gulonic acid-producing strain *Ketogulonigenium vulgare* LMP P-20356 in L-sorbose/CSL medium", Applied Microbiology and Biotechnology, vol. 65, No. 2, Aug. 2004, pp. 163-167.
International Search Report.

* cited by examiner

*Primary Examiner*—Ruth Davis
*Assistant Examiner*—Sheridan R MacAuley
(74) *Attorney, Agent, or Firm*—Nixon & Vanderhye P.C.

(57) ABSTRACT

The present invention provides a process for the production of vitamin C from a substrate, such as for instance L-sorbosone using a microorganism belonging to the genus *Ketogulonicigenium*.

7 Claims, No Drawings

MICROBIAL PRODUCTION OF VITAMIN C

This application is the US national phase of international application PCT/EP2005/000622 filed 22 Jan. 2005 which designated the U.S. and claims benefit of EP 04002074.5, dated 30 Jan. 2004, the entire content of which is hereby incorporated by reference.

The present invention relates to the microbial production of L-ascorbic acid (vitamin C).

Vitamin C, which is one of very important and indispensable nutrient factors for human beings, has been commercially produced by the so-called "Reichstein method", which is well known as a technologically established process. This method, however, comprises a number of complex steps and any improvement in the overall yield is difficult to achieve. Therefore, there have been a number of proposals, which contemplate a reduction in the number of steps and/or an improvement in the overall yield.

The present invention provides a process for the production of vitamin C comprising converting a substrate into vitamin C in a medium using a microorganism belonging to the genus *Ketogulonicigenium*.

Conversion of the substrate into vitamin C means that the conversion of the substrate resulting in vitamin C is performed by the microorganism belonging to the genus *Ketogulonicigenium*, i.e. the substrate may be directly converted into vitamin C. Said microorganism is cultured under conditions which allow such conversion from the substrate as defined above, e.g. directly contacting the microorganism with the substrate. The microorganism may be further used, for instance, in the form of resting cells, acetone treated cells, lyophilized cells, immobilized cells and the like to act directly on the substrate. Any means per se known as a method in connection with the incubation technique for microorganisms may be adopted through the use of aeration, preferably agitated submerged fermenters. The preferred cell concentration range for carrying out the reaction is from about 10 mg to about 700 mg of wet cell per ml, more preferably from about 30 mg to about 500 mg of wet cell per ml.

A medium as used herein may be any suitable medium for the production of vitamin C. Typically, the medium is an aqueous medium comprising for instance salts, substrate(s), and a certain pH.

As substrate may be used a carbon source such as, for example, D-sorbitol, L-sorbose, L-sorbosone, L-gulose or L-gulono-gamma-lactone. Preferably, the substrate is selected from D-sorbitol, L-sorbose or L-sorbosone, more preferably L-sorbosone.

Suitable microorganisms belonging to the genus *Ketogulonicigenium* may be for instance selected from *Ketogulonicigenium robustum*, *Ketogulonicigenium vulgare* or mutants thereof which are capable of performing the conversion of the substrate to vitamin C as of the present invention. In one aspect of the present invention, the microorganism belonging to the genus *Ketogulonicigenium* is selected from *Ketogulonicigenium robustum*, *Ketogulonicigenium vulgare* or mutants thereof excluding *Ketogulonicigenium vulgare* DSM 4025 or mutants thereof.

In one embodiment, the present invention provides a process for the production of vitamin C from L-sorbosone which comprises contacting a microorganism which is selected from *Ketogulonicigenium robustum*, *Ketogulonicigenium vulgare* or mutants thereof with L-sorbosone in a reaction mixture and isolating and purifying vitamin C from the reaction mixture.

It is understood that the microorganisms "*Ketogulonicigenium robustum*" and "*Ketogulonicigenium vulgare*" also include synonyms or basonyms of such species having the same physiological properties, as defined by the International Code of Nomenclature of Prokaryotes.

As used herein, "mutants" of the microorganisms mentioned above refer to microorganisms which are altered in their genomic sequences which are capable of the conversion of a substrate such as for instance L-sorbosone to vitamin C as provided by the process of the present invention. Mutants may be obtained by any convenient means including, for example, chemical and UV mutagenesis, followed by screening or selection for a desired phenotype, construction of dysfunctional genes in vitro by recombinant techniques used to replace the intact counterparts of the genes in the genome of the microorganism, by single and double cross-over recombinations, and other well known techniques. See, Sambrook, et al., Molecular Cloning, A Laboratory Manual, 2nd Ed., Cold Spring Harbor Laboratory Press (1989) and, Harwood and Cutting, Molecular Biology Methods For *Bacillus*, John Wiley and Sons (1990), pp. 27-74. Suitable mutagens include, but are not limited to, ultraviolet-ray, X-ray, γ-ray and chemical mutagens such as nitrogen mustard or N-methyl-N'-nitro-N-nitrosoguanidine. Furthermore, a mutant can be obtained by isolating a clone occurring by spontaneous mutation thereof in any of the ways per se well known for the purpose by one skilled in the art.

In a preferred embodiment, the microorganisms as used for the process of the present invention are selected from the group consisting of *K. robustum* NRRL B-21627, *K. vulgare* NRRL B-30035, *K. vulgare* NRRL B-30036, *K. vulgare* NRRL B-30037N and the respective mutants thereof.

*K. robustum* NRRL B-21627 is described in U.S. Pat. No. 5,834,231. Strains *K. vulgare* NRRL B-30035, *K. vulgare* NRRL B-30036 and *K. vulgare* NRRL B-30037N are described in U.S. Pat. No. 6,316,231 B 1. These strains are publicly available from the Agricultural Research Culture Collection (NRRL), 1815 N. University Street, Peoria, Ill. 61604, USA.

In one embodiment the present invention provides a process for the production of vitamin C from L-sorbosone which comprises contacting a microorganism belonging to the genus *Ketogulonicigenium* with L-sorbosone in a reaction mixture and isolating and purifying vitamin C from the reaction mixture.

As used herein, "contacting a microorganism with L-sorbosone in a reaction mixture" includes cultivation of the microorganism in a medium containing L-sorbosone. The microorganism may be further used, for instance, in the form of resting cells, acetone treated cells, lyophilized cells, immobilized cells and the like to act directly on the substrate, i.e. L-sorbosone. Any means per se known as a method in connection with the incubation technique for microorganisms may be adopted through the use of aeration, preferably agitated submerged fermenters. The preferred cell concentration range for carrying out the reaction is from about 10 mg to about 700 mg of wet cell per ml, more preferably from about 30 mg to about 500 mg of wet cell per ml.

A suitable "reaction mixture" could be water or any nutrient medium known in the art for the cultivation of the microorganism. Such nutrient medium includes a carbon source, a nitrogen source and other inorganic salts, which can be utilized by the microorganism. Various nutrient materials which are generally used for the better growth of microorganisms may suitably be included in the medium.

Examples of such nutrients as assimilable carbon sources include, but are not limited to, glycerol, D-mannitol, erythritol, ribitol, xylitol, arabitol, inositol, dulcitol, D-ribose, D-fructose, D-glucose and sucrose. Examples of digestible nitrogen sources such as organic substances, include, but are not limited to, peptone, yeast extract, baker's yeast, urea, amino acids and corn steep liquor. Various inorganic substances may also be used as nitrogen sources, for example nitrates and ammonium salts. Furthermore, the culture medium usually contains inorganic salts, for example, magnesium sulfate, potassium phosphate and calcium carbonate.

Cultivation of the microorganisms of the present invention may be conducted at a pH of about 4.0 to about 9.0, wherein a pH of about 5.0 to about 8.0 may preferably be maintained. The cultivation period varies depending on the pH, temperature and nutrient medium to be used, and is preferably about 1 to 5 days, most preferably about 1 to 3 days. The preferred temperature for carrying out the process of the present invention is a temperature of about 13 to about 36° C., more preferably of about 18 to about 33° C.

In one embodiment the process of the present invention is carried out at a pH of about 4.0 to about 9.0 and at a temperature of about 13 to about 36° C. Preferably, a pH of about 5.0 to about 8.0 and a temperature of about 18 to about 33° C. is used for carrying out the inventive process.

Although the concentration of the substrate such as for instance L-sorbosone may vary with the reaction conditions, the reaction is preferably carried out at substrate concentrations of about 2 to about 120 mg/ml, more preferably at concentrations of about 4 to about 100 mg/ml. In one embodiment the process of the present invention is carried out at L-sorbosone concentrations of about 2 to about 120 mg/ml, more preferably at concentrations of about 4 to about 100 mg/ml.

The vitamin C thus produced and accumulated in the reaction mixture may be separated and purified by any per se known conventional method which suitably utilized the property of the product, and it may be separated as the free acid or as a salt of sodium, potassium, calcium, ammonium or the like.

Specifically, the separation may be performed by any suitable combination or repetition of the following steps: by the formation of a salt, by using differences in properties between the product and the surrounding impurities, such as solubility, absorbability and distribution coefficient between the solvents, by absorption, for example on ion exchange resin. Any of these procedures alone or in combination constitute a convenient means for isolating the product. The product thus obtained may further be purified in a conventional manner, for example, by re-crystallization or chromatography.

According to the present invention, the improvement in terms of the reduction in the number of steps is very significant because it leads to one step pathway directed to the production of the vitamin C from the substrate such as for instance L-sorbosone.

In the following Example, the process of the present invention will be illustrated in more detail.

EXAMPLE 1

Production of Vitamin C from L-sorbosone with Resting Cell System

*K. robustum* NRRL B-21627 and *K. vulgare* strains NRRL B-30035, NRRL B-30036 and NRRL B-30037N were cultivated on Triptic Soy Agar (Difco, Becton, Dickinson and Company, Sparks, Md., USA) at 30° C. for 3 days. The cells were harvested from the plate and suspended into 1 ml of 50 mM potassium phosphate buffer (pH 7.0) and washed twice with the same buffer. The optical density of the cell suspensions at 600 nm were 12.2, 12.5, 16.2 and 11.2 for strains NRRL B-21627, NRRL B-30035, NRRL B-30036 and NRRL B-30037, respectively. These numbers corresponded to 31.7, 32.5, 42.1 and 29.1 mg of wet cell weight per ml, respectively.

The reaction mixture (5 ml in test tube) contained 0.9 ml of the cell suspension and 0.1 ml of 50 mg/ml L-sorbosone in 50 mM potassium phosphate buffer (pH 7.0). The reaction was started by the addition of the cell suspension. The reaction mixture was incubated at 30° C. and with 180 rpm on a reciprocal shaker for 3 hours. After the reaction, the reaction mixture was centrifuged at 8,000×g for 10 min to obtain the supernatant. The vitamin C content in the supernatant was measured with HPLC:

Column: YMC-Pack Polyamine II (150×4.6 mm i.d.), YMC Co. Ltd, Kyoto, Japan,

Eluent: 50 mM $NH_4H_2PO_4$/Acetonitrile=30/70

Flow rate: 1 ml/min,

Detection: UV absorption at 250 nm

The retention time of vitamin C under the HPLC conditions above was 7.7 min. The reaction product with all the strains tested was confirmed to be vitamin C with this HPLC analysis.

Table 1 shows the quantity of vitamin C produced by strains NRRL B-21627, NRRL B-30035, NRRL B-30036 and NRRL B-30037N.

TABLE 1

| Vitamin C production from L-sorbosone | |
|---|---|
| Strain | Vitamin C produced (mg/ml) |
| *K. robustum* NRRL B-21627 | 0.21 |
| *K. vulgare* NRRL B-30035 | 0.44 |
| *K. vulgare* NRRL B-30036 | 0.36 |
| *K. vulgare* NRRL B-30037N | 0.46 |

The invention claimed is:

1. A process for the production of vitamin C from L-sorbosone using a microorganism belonging to the genus *Ketogulonicigenium*, said process comprising contacting cells consisting of a microorganism belonging to the genus *Ketogulonicigenium* in a reaction medium containing L-sorbosone and isolating the produced vitamin C from the reaction mixture and optionally further purifying the produced vitamin C.

2. The process according to claim 1, wherein the microorganism is selected from the group consisting of *Ketogulonicigenium robustum, Ketogulonicigenium vulgare*.

3. The process according to claim 1, wherein the microorganism is selected from the group consisting of *Ketogulonicigenium robustum* NRRL B-21627, *Ketogulonicigenium vulgare* NRRL B-30035, *Ketogulonicigenium vulgare* NRRL B-30036 and *Ketogulonicigenium vulgare* NRRL B-30037.

4. The process according to claim 1, wherein the process is carried out at a pH of about 4.0 to about 9.0 and at a temperature of about 13 to about 36° C.

5. The process according to claim 1, wherein the process is carried out at a pH of about 5.0 to about 8.0 and at a temperature of about 18 to about 33° C.

6. The process according to claim 1, wherein the process is carried out at a L-sorbosone concentration of about 2 to about 120 mg/ml.

7. The process according to claim 6, wherein the process is carried out at a L-sorbosone concentration of about 4 to about 100 mg/ml.

* * * * *